(12) United States Patent
Durrance et al.

(10) Patent No.: US 8,323,435 B2
(45) Date of Patent: Dec. 4, 2012

(54) MECHANICAL FASTENING SYSTEM FOR AN ARTICLE

(75) Inventors: Debra H. Durrance, Appleton, WI (US); Robert L. Popp, Hortonville, WI (US); Marcille F. Ruman, Oshkosh, WI (US); Alexander J. Neeb, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2269 days.

(21) Appl. No.: 10/210,260

(22) Filed: Jul. 31, 2002

(65) Prior Publication Data

US 2004/0020579 A1    Feb. 5, 2004

(51) Int. Cl.
*B29C 65/72* (2006.01)

(52) U.S. Cl. ........ 156/163; 156/164; 156/229; 156/290; 156/291; 156/324; 156/324.4

(58) Field of Classification Search .................... 156/66, 156/229, 290, 291, 163, 164, 324, 324.4; 24/442–452; 604/385.21, 391; 428/99; 442/327–329, 394–399, 400–402, 408–409
See application file for complete search history.

(56) References Cited

U.S. PATENT DOCUMENTS

| | | | |
|---|---|---|---|
| 2,957,512 A | 10/1960 | Wade et al. |
| 3,319,307 A | 5/1967 | Marforio |
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,577,607 A | 5/1971 | Ikoma et al. |
| 3,692,618 A | 9/1972 | Dorschner et al. |
| 3,694,867 A | 10/1972 | Stumpf |
| 3,802,817 A | 4/1974 | Matsuki et al. |
| 3,943,981 A | 3/1976 | DeBrabander |
| 4,100,324 A | 7/1978 | Anderson et al. |
| 4,205,679 A | 6/1980 | Repke et al. |
| 4,209,563 A | 6/1980 | Sisson |
| 4,340,563 A | 7/1982 | Appel |
| 4,610,680 A | 9/1986 | LaFleur |
| 4,615,695 A | 10/1986 | Cooper |
| 4,640,726 A | 2/1987 | Sallee et al. |
| 4,663,220 A | 5/1987 | Wisneski et al. |
| 4,699,622 A | 10/1987 | Toussant et al. |
| 4,704,116 A | 11/1987 | Enloe |
| 4,705,710 A | 11/1987 | Matsuda |
| 4,714,096 A | 12/1987 | Guay |

(Continued)

FOREIGN PATENT DOCUMENTS

EP    0 217 032 A2    8/1987

(Continued)

OTHER PUBLICATIONS

Internation Search Report for PCT/US 03/15955 dated Sep. 2, 2003.

(Continued)

*Primary Examiner* — Christopher Schatz
(74) *Attorney, Agent, or Firm* — Armstrong Teasdale LLP

(57) ABSTRACT

A mechanical fastening system for products, for example, an absorbent article such as infant training pants, in which the mechanical fastening system is a hook-and-loop type fastening system on the garment in which the loop material is a nonwoven material laminate which has been post bonded after the laminate has been constructed.

20 Claims, 12 Drawing Sheets

U.S. PATENT DOCUMENTS

| | | |
|---|---|---|
| 4,741,949 A | 5/1988 | Morman et al. |
| 4,761,318 A | 8/1988 | Ott et al. |
| 4,803,117 A | 2/1989 | Daponte |
| 4,940,464 A | 7/1990 | Van Gompel et al. |
| 965,122 A | 10/1990 | Morman |
| 4,981,747 A | 1/1991 | Morman |
| 5,032,122 A | 7/1991 | Noel |
| 5,046,272 A | 9/1991 | Vogt et al. |
| 5,087,253 A | 2/1992 | Cooper |
| 5,104,116 A | 4/1992 | Pohjola |
| 5,116,662 A | 5/1992 | Morman |
| 5,224,405 A | 7/1993 | Pohjola |
| 5,226,992 A | 7/1993 | Morman |
| 5,256,231 A | 10/1993 | Gorman et al. |
| 5,326,612 A | 7/1994 | Goulait |
| 5,370,634 A | 12/1994 | Ando et al. |
| 5,407,439 A | 4/1995 | Goulait |
| 5,595,567 A | 1/1997 | King et al. |
| 5,614,281 A | 3/1997 | Jackson et al. |
| 5,615,460 A | 4/1997 | Weirich et al. |
| 5,616,934 A | 4/1997 | Dennison et al. |
| 5,624,427 A | 4/1997 | Bergman et al. |
| 5,628,741 A | 5/1997 | Buell et al. |
| 5,647,864 A * | 7/1997 | Allen et al. ............ 604/391 |
| 5,656,111 A * | 8/1997 | Dilnik et al. ............ 156/66 |
| 5,669,900 A | 9/1997 | Bullwinkel et al. |
| 5,763,041 A * | 6/1998 | Leak et al. ............ 428/100 |
| 5,766,389 A | 6/1998 | Brandon et al. |
| 5,830,206 A | 11/1998 | Larsson |
| 5,830,298 A * | 11/1998 | Jackson ............ 156/66 |
| 5,855,574 A | 1/1999 | Kling et al. |
| 5,888,607 A | 3/1999 | Seth et al. |
| 5,891,547 A | 4/1999 | Lawless |
| 5,897,545 A | 4/1999 | Kline et al. |
| 5,897,547 A | 4/1999 | Schmitz |
| 5,961,761 A * | 10/1999 | Heindel et al. ............ 156/163 |
| 5,997,981 A | 12/1999 | McCormack et al. |
| 6,027,485 A | 2/2000 | Matsushita et al. |
| B14704116 I5 | 10/2000 | Enloe |
| 6,146,738 A | 11/2000 | Tsuji et al. |
| 6,287,287 B1 | 9/2001 | Elsberg |
| 6,302,871 B1 | 10/2001 | Nakao et al. |
| 6,328,725 B2 | 12/2001 | Fernfors |
| 6,329,016 B1 | 12/2001 | Shepard et al. |
| 6,332,250 B1 | 12/2001 | Igaue et al. |
| 6,461,344 B1 | 10/2002 | Widlund et al. |
| 2004/0002691 A1 * | 1/2004 | Popp et al. ............ 604/387 |

FOREIGN PATENT DOCUMENTS

| | | |
|---|---|---|
| EP | 0 217 032 A3 | 8/1987 |
| EP | 0 217 032 B1 | 8/1987 |
| EP | 0812584 A2 | 5/1997 |
| EP | 1 066 961 A1 | 1/2001 |
| EP | 1 279 348 A1 | 1/2003 |
| EP | 1279348 * | 1/2006 |
| FR | 1375254 | 9/1963 |
| WO | WO 00/35398 | 6/2000 |
| WO | WO 00/37009 | 6/2000 |
| WO | WO 01/80680 * | 11/2001 |
| WO | WO 01/87206 A1 | 11/2001 |

OTHER PUBLICATIONS

Written Opinion for PCT/US 03/15955, dated Jul. 6, 2004, 7 pages.

* cited by examiner

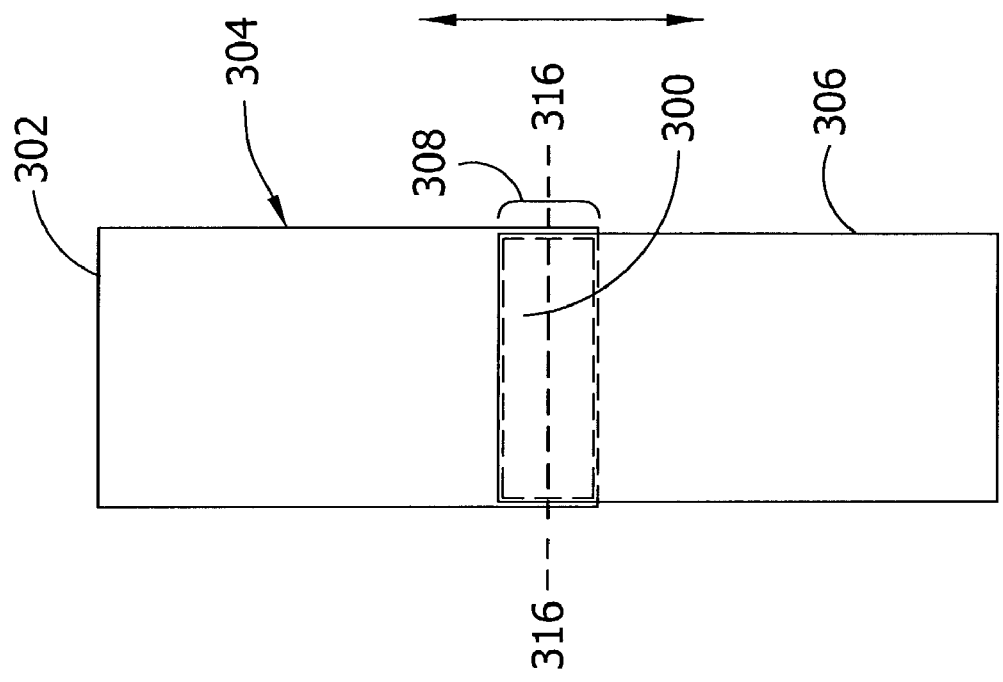
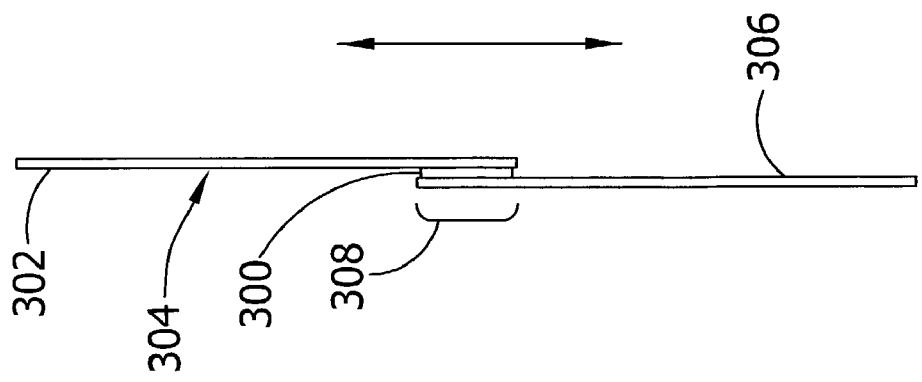

MECHANICAL FASTENING SYSTEM FOR AN ARTICLE

BACKGROUND OF THE INVENTION

The present invention pertains to a mechanical fastening system for application to many products, for example, absorbent articles, such as training pants, diapers, incontinence garments and the like.

Such absorbent articles generally comprise a liquid-impermeable barrier sheet, a liquid permeable body side liner and an absorbent medium between them. They generally include some type of attaching system for fitting the article on the wearer. In many such applications, the fastening system is preferably refastenable so that the article can be temporarily removed and then refastened on the wearer.

Common forms of mechanical attachment systems are the so called hook-and-loop system which comes in various forms and has both advantages and disadvantages in its application to such absorbent articles. For example, particularly with diapers, the fasteners are secured to both sides of the garment on the front and back thereof, generally in such a manner that the back portion of the fasteners on each side are pulled over the front portion to secure the garment on the wearer. In typical such products, the loop material is generally non-extensible and is attached to the surface of the garment. The hook material is generally attached to an extensible substrate so that it can be positioned on the loop material for adjustment to the size and shape of the wearer of the garment.

A disadvantage of this type of hook-and-loop system is the tendency of the hooks to separate from the loop material when the wearer is active, such as when stooping or bending as is common with a child. This disengagement failure results in the garment coming loose from the wearer (with possible leakage resulting) thus requiring it to be refastened, if possible. This produces an undesirable inconvenience and disadvantage of such a mechanical fastening system for such applications.

Another disadvantage of this type of hook-and-loop system is the generally high cost of the materials, which tends to constrain the size and construction of the fastening elements used in disposable applications and may constitute a compromise in performance. Woven or knitted loop materials are well-known and commonly available, but are very expensive. Nonwoven loop materials are much less costly, but are not available widely or with a wide range of properties or applicability. Nonwoven loop materials are also generally less durable than woven or knitted loop materials, and frequently suffer delamination or other damage during use, which may contribute to disengagement failure.

SUMMARY OF THE INVENTION

The present invention overcomes the above-described difficulties and disadvantages associated with such prior art mechanical fastening systems by providing a hook-and-loop fastening system in which the loop material is a nonwoven laminate with a relatively high z-directional strength bonding between the laminate layers. This loop material can be used for making many products such as a disposable training pant, a disposable diaper, as well as articles which are not absorbent and/or which are not garments.

In a preferred embodiment of the present invention, a mechanical fastening system for an article is provided, comprising: a first fastening component disposed on the article, the first fastening component comprising a nonwoven loop laminate material made with post bonding in at least a portion of the material; and a second fastening component disposed on the article so as to be engageable with the first fastening component, the second fastening component comprising a hook material. The nonwoven loop laminate material may be made by elongating a nonwoven facing in a machine direction so as to neck down in the cross machine direction and then attaching the facing to a base material and which laminate is post bonded. Alternatively, the loop laminate material may be made by laminating a nonwoven facing to a base material that has been elongated in the machine direction so as to gather when the elongating force is released, and then which laminate is post bonded, either relaxed or under tension. Preferably at least 25% of the landing area of the first fastening member is post bonded, with bond density of between 1% and 75% of the landing area.

The nonwoven loop laminate material may comprise an oriented nonwoven loop laminate material produced by application of a force causing constituent fibers of the nonwoven loop laminate material to become oriented in a direction of the applied force with or without substantial necking or gathering of the nonwoven loop laminate material in a direction perpendicular to the applied force. The first fastening component may be stabilized by laminating the oriented nonwoven loop laminate material to a base material, such as a polymer film. The constituent fibers of the nonwoven loop laminate material may be oriented in the machine direction or in the cross machine direction. It may also have been stabilized by thermally treating the material.

Alternatively, the loop laminate material may comprise a stretchable loop material, the stretchable loop material being extensible and elastomeric during use. The stretchable loop material may further comprise a nonwoven web stretch bonded to an elastomeric layer. The stretchable loop material may further comprise a mechanically prestrained laminate. The stretchable loop material may form part or all of the outer layer.

Alternatively, the loop laminate material may comprise a multi-directional stretchable loop material, the stretchable loop material being extensible and elastomeric during use in first and second substantially perpendicular directions. The multi-directional stretchable loop material may further comprise a nonwoven web stretch bonded to an elastomeric film. The multi-directional stretchable loop material may further comprise a mechanically prestrained laminate. The multi-directional stretchable loop material may form part or all of the outer or inner layer.

According to a method of the present invention, a method of forming a post bonded loop laminate material suitable for use in a hook and loop fastening system for an article is provided, comprising: providing a first layer of material comprising a nonwoven web of loop material; laminating the first layer of material to a second layer of material to form a nonwoven loop laminate material; and post bonding the nonwoven loop laminate material to form the post bonded loop laminate material. Additionally, the laminate can be stretched in one or more directions or allowed to retract in one or more directions prior to post bonding.

In these and other anticipated embodiments, the post bonding process may be done after lamination as a subsequent step in the process sequence, as a separate step prior to delivery of the laminate into a product assembly process, or as a step in the product assembly process.

BRIEF DESCRIPTION OF THE DRAWINGS

The above-mentioned and other features of the present invention, and the manner of obtaining them, will become more apparent and the invention itself will be better understood by reference to the following description of the embodiments of the invention taken in conjunction with the accompanying drawings, wherein:

FIG. 12 is a side elevation view of an exemplary test specimen.

FIG. 13 is a top plan view of the specimen of FIG. 12.

Corresponding reference characters indicate corresponding parts throughout the drawings.

DEFINITIONS

Figure 1:
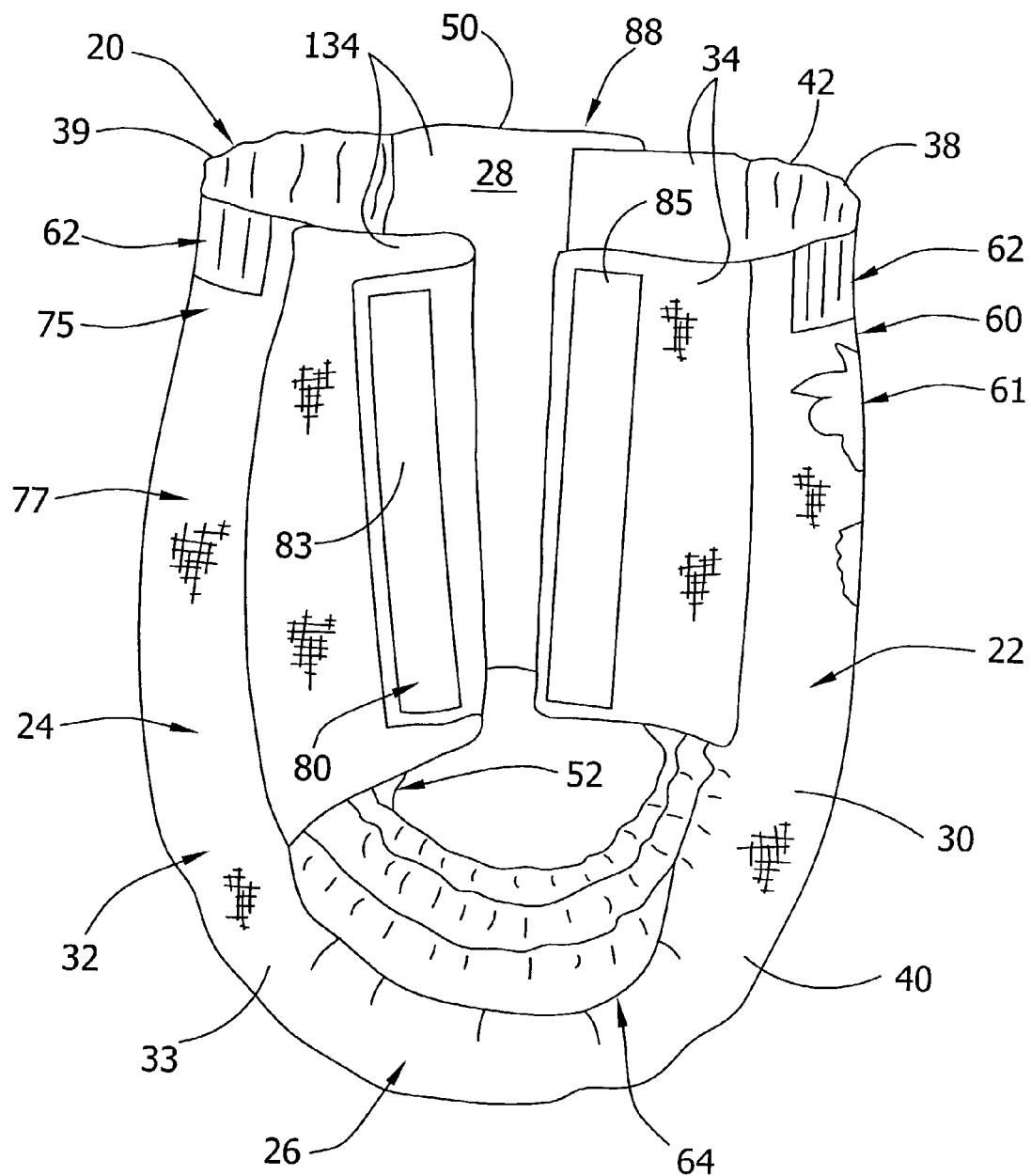
FIG. 1 illustrates a side view of a training pant where the fastening system is shown engaged on one side of the training pant and disengaged on the other side of the training pant.

Within the context of this specification, each term or phrase below will include the following meaning or meanings.

"Attached to" and variations thereof are intended to mean that one element can be integral with another element, or that one element can be a separate structure bonded to or placed with or placed near another element.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Creping" and "creped" refer to a method of gathering a material in the machine direction to allow it some extensibility in that direction, which typically is accompanied by a reduction in the length of the material.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to a material or composite that is stretchable or capable of being elongated in at least one direction, but which may not have sufficient recovery to be considered elastic.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Landing area" is that portion of a loop fastening component, often referred to as a female fastening component, that is intended to engage with the hook, or male, fastening component. The landing area is often, but need not be, substantially larger than the surface area of the hook fastening area. This is especially important when the loop component is an integral part of a larger structure within a garment, such as part of a top sheet rather than a separately applied material.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

Figure 2:
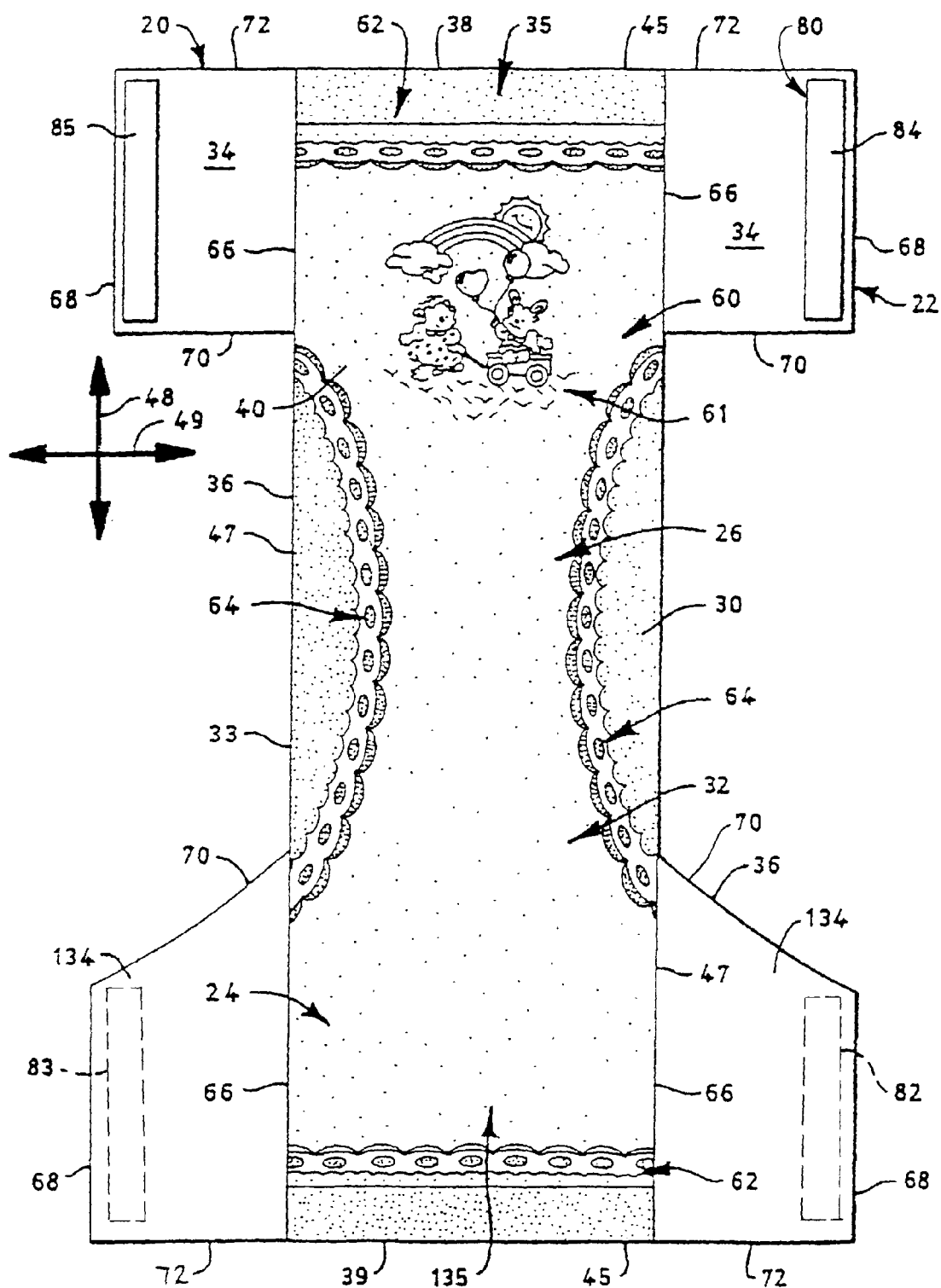
FIG. 2 illustrates a plan view of the training pant shown in FIG. 1 in an unfastened, stretched and laid flat condition, and showing the surface of the training pant that faces away from the wearer.
Figure 3:
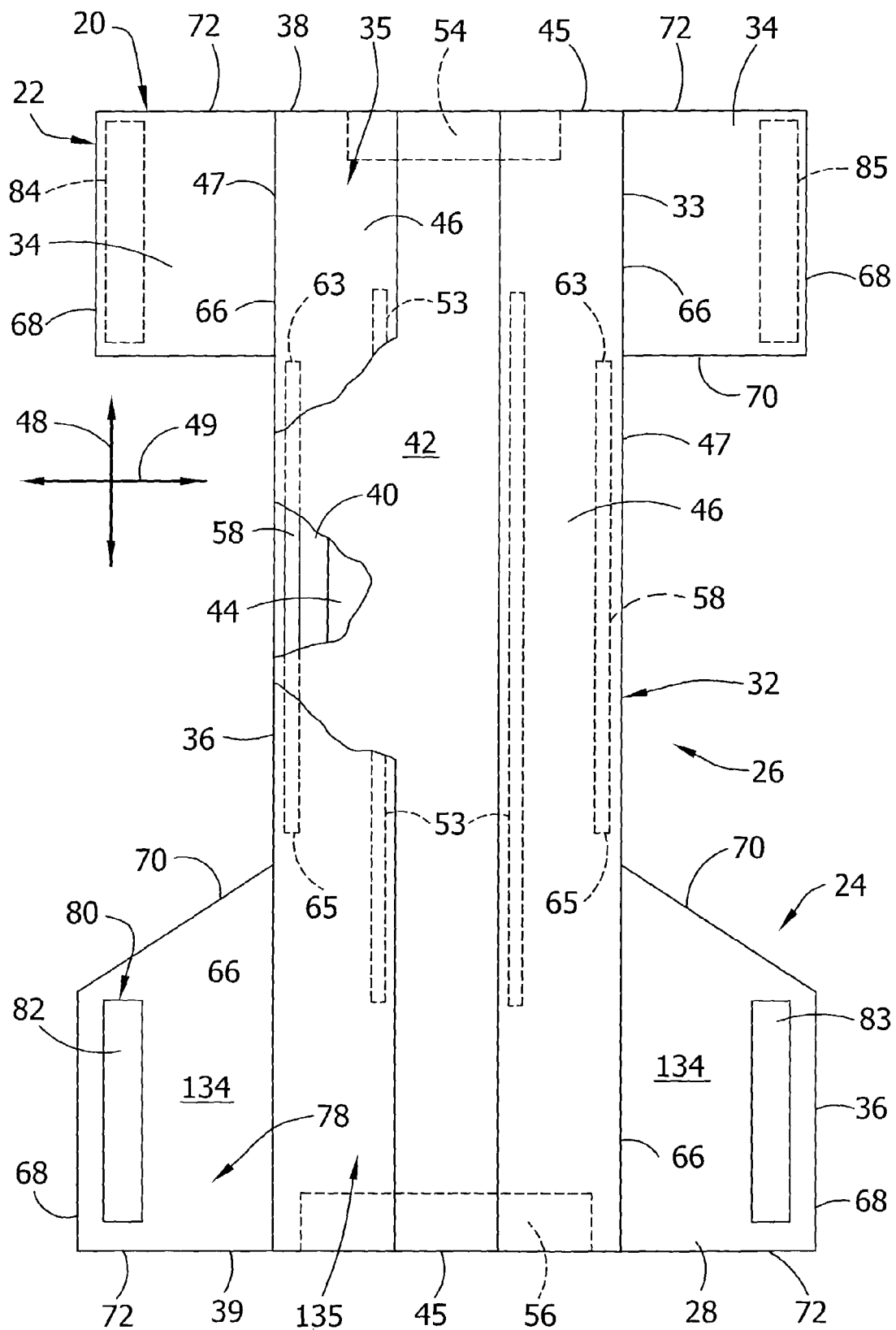
FIG. 3 illustrates a plan view similar to FIG. 2, but showing the surface of the training pant that faces the wearer when the training pant is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Post bonding" refers to overbonding at least a portion of a previously formed laminate such as by use of ultrasonic bonders, thermal bonders, through-air bonders and the like.

"Prestrained laminate" refers to a laminate in which one of the webs forming the laminate is a nonelastic web that has been subjected to some degree of at least localized mechanical stretching to permanently elongate portions of the non-elastic web which is then laminated to an elastic base material, as disclosed, for example, in U.S. Pat. Nos. 5,628,741 to Buell et al. and 6,302,871 to Nakao et al.

"Refastenable" refers to the property of two elements being capable of attachment, separation, and subsequent reattachment.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Necking" or "neck stretching" interchangeably refer to a method of elongating a material, generally in the machine direction, to reduce its width in a controlled manner to a desired degree. The controlled stretching may take place under cool conditions, at room temperature, or at an elevated temperature, and is limited to an increase in overall dimension in the direction of elongation up to the elongation required to break the fabric, which in most cases is about 1.2 to 1.4 times the original fabric length.

"Oriented material" refers to a material in which mechanical drawing of the material has resulted in alignment of the fibers constituting the material in a direction generally parallel to the direction of the applied force.

"Reversibly necked material" refers to a necked material that has been treated while necked to impart memory to the material so that, when a force is applied to extend the material to its pre-necked dimensions, the necked and treated portions will generally recover to their necked dimensions upon termination of the force. One form of treatment is the application of heat. Generally speaking, extension of the reversibly necked material is substantially limited to extension to its pre-necked dimensions. Therefore, unless the material is elastic, extension too far beyond its pre-necked dimensions will result in material failure. A reversibly necked material may include more than one layer. For example, multiple layers of spunbonded web, multiple layers of meltblown web, multiple layers of bonded carded web or any other suitable combination or mixtures thereof.

"Rupture" means the breaking or tearing apart of a material; in tensile testing, the term refers to the total separation of a material into two parts either all at once or in stages, or the development of a hole in some materials.

"Spunbonded" refers to small diameter fibers which are formed by extruding molten thermoplastic material as filaments from a plurality of fine, usually circular capillaries of a spinnerette with the diameter of the extruded filaments then being rapidly reduced as disclosed, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann and U.S. Pat. No. 3,542,615 to Dobo et al. Spunbond fibers are generally continuous and larger than 7 microns, more particularly, they are usually between about 15 and 50 microns.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300-600 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

"Z-directional strength" means the strength between the laminates that holds the laminates together as well as the ability of a nonwoven facing in a laminate to resist rupture.

These terms may be defined with additional language in the remaining portions of the specification.

DETAILED DESCRIPTION OF THE PREFERRED EMBODIMENTS

FIG. 1 representatively illustrates one embodiment of training pant 20 in a partially fastened condition. The training pant 20 comprises an absorbent body 32 and a fastening system 80. The absorbent body 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent body 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

The illustrated absorbent body 32 comprises a rectangular composite structure 33, a pair of transversely opposed front side panels 34, and a pair of transversely opposed back side panels 134. The composite structure 33 and side panels 34 and 134 may be integrally formed or comprise two or more separate elements, as shown in FIG. 1. The illustrated composite structure 33 comprises an outer cover 40, a body side liner 42 (FIG. 3) which is connected to the outer cover in a superposed relation, an absorbent assembly 44 (FIG. 3) which is located between the outer cover and the body side liner, and a pair of containment flaps 46 (FIG. 3). The illustrated composite structure 33 has opposite linear end edges 45 that form portions of the front and back waist edges 38 and 39, and opposite linear side edges 47 that form portions of the side edges 36 of the absorbent body 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent body 32 includes the transversely opposed front side panels 34 and a front center panel 35 (FIGS. 2 and 3) positioned between and interconnecting the side panels. The back waist region 24 of the absorbent body 32 includes the transversely opposed back side panels 134 and a back center panel 135 (FIGS. 2 and 3) positioned between and interconnecting the side panels. The waist edges 38 and 39 of the absorbent body 32 are configured to encircle the waist of the wearer when worn and provide the waist opening 50 which defines a waist perimeter dimension. Portions of the transversely opposed side edges 36 in the crotch region 26 generally define the leg openings 52. The waist regions 22 and 24 jointly define a waistband 75 (FIGS. 1 and 4) that peripherally surrounds the waist opening 50 of the pant 20. The waist regions 22 and 24 also jointly define a hip section 77 (FIGS. 1 and 4) that encircles the pant 20 and is disposed between the waistband 75 and the leg openings 52.

The absorbent body 32 is configured to contain and/or absorb any body exudates discharged from the wearer. For example, the absorbent body 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent body 32, and can extend longitudinally along the entire length of the absorbent body or may only extend partially along the length of the absorbent body. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 3). The waist elastic members 54 and 56 can be operatively joined to the outer cover 40 and/or body side liner 42 along the opposite waist edges 38 and 39, and can extend over part or all of the waist edges, such that the waist elastic members are disposed in the waistband 75 in the fully assembled pant.

The leg elastic members 58 are desirably operatively joined to the outer cover 40 and/or body side liner 42 along the opposite side edges 36 and positioned in the crotch region 26 of the training pant 20. The leg elastic members 58 can be longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. DuPont de Nemours and Company, Wilmington, Del. U.S.A.

In particular embodiments, the waist elastic members 54 and 56 can be formed of retractive materials. For example, the waist elastic members 54 and 56 can be formed of an elastomeric material that is adapted to retract upon activation by a source of heat such as disclosed in U.S. Pat. No. 4,640,726.

The outer cover 40 desirably comprises a material that is substantially liquid impermeable, and can be elastic or inelastic. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. While it is not a necessity for the outer layer to be liquid permeable, it is desired that it provides a relatively cloth-like texture to the wearer. The outer cover may also be made of a stretchable material made with a nonwoven facing and an elastic base material as provided by this invention, constituting an integral and functional loop material as the entire outer surface of the product.

The inner layer of the outer cover 40 can be both liquid and vapor impermeable, or can be liquid impermeable and vapor permeable. The inner layer is desirably manufactured from a thin film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Packaging of Schaumburg, Ill. U.S.A. If the outer cover 40 is a single layer of material, it can be embossed and/or matte finished, providing a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated fly openings for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal centerline of the training pant 20.

The liquid permeable body side liner 42 is illustrated as overlying the outer cover 40 and absorbent assembly 44, and may but need not have the same dimensions as the outer cover 40. The body side liner 42 is desirably compliant, soft feeling, and non-irritating to the child's skin. Further, the body side liner 42 can be less hydrophilic than the absorbent assembly 44, to present a relatively dry surface to the wearer and permit liquid to readily penetrate through its thickness. Alternatively, the body side liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the body side liner 42 and absorbent assembly 44 to achieve the desired wetness sensation or leakage performance.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel® N-62 from Hodgson Textile Chemicals of Mount Holly, N.C. U.S.A. and GLUCOPON® 220UP from The Cognis Group of Ambler, Pa. in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the body side liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulose fluff, mixed with particles of a high-absorbency material commonly known as superabsorbent material. In a particular embodiment, the absorbent assembly 44 comprises a matrix of cellulose fluff, such as wood pulp fluff, and superabsorbent hydrogel-forming particles. The wood pulp fluff can be exchanged with synthetic, polymeric, meltblown fibers or short cut homofilament or bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent body 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent body 32. These transversely opposed front side panels 34 and transversely opposed back side panels 134 can be permanently bonded along attachment lines 66 to the composite structure 33 of the absorbent body 32 in the respective front and back waist regions 22 and 24. More particularly, as shown best in FIGS. 2 and 3, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as a portion of a component of the composite structure 33. For example, the side panels can comprise a generally wider portion of the outer cover, the body side liner, and/or another component of the absorbent body.

The side panels 34 and 134 preferably have elastic properties with sufficient extensibility to allow the wearer to pull the product up without having to open the fasteners on the pant. The side panels 34 and 134 also preferably provide sufficient retraction tension at extensions normally seen during wear to ensure good fit during wear without adjusting the fastener position. If the outer cover 40, as described above, comprises an elastic material, the side panels 34 and 134 may require less extensibility. Alternately, the pant may have an all-over stretch material across the entire width of the pant, comprising the outer cover 40 and side panels 34 and 134 as a single material component. The extension requirements of the side panels 34 and 134 are determined by the desired fit range for the product and the interaction with extension of other components, e.g., outer cover 40.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent body 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably although not necessarily parallel to the transverse axis 49. The waist end edges 72 of the front side panels 34 form part of the front waist edge 38 of the absorbent body 32, and the waist end edges 72 of the back side panels 134 form part of the back waist edge 39 of the absorbent body.

In particular embodiments for improved fit and appearance, the side panels 34 and 134 desirably have an average length dimension measured parallel to the longitudinal axis 48 that is about 15 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown). The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate, a neck-bonded laminate, a reversibly necked laminate, or a stretch-bonded laminate material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or body side liner 42; mechanically prestrained materials; or extensible but inelastic materials.

In particular embodiments, one or more of the side panels 34 and 134 can be formed of retractive materials. For example, the side panels 34 and 134 can be formed of an elastomeric material that is adapted to retract upon activation by a source of heat, such as disclosed in U.S. Pat. No. 4,640,726.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage engaging elements of the second fastening components 84 and 85.

In one particular embodiment, the first fastening components 82 and 83 each comprise hook type fasteners and the second fastening components 84 and 85 each comprise complementary fasteners formed of a stretchable nonwoven loop material that has been post bonded as described herein. In another particular embodiment, the first fastening components 82 and 83 each comprise fasteners formed of a multi-directional or uni-directional stretchable nonwoven loop material which has been post bonded and the second fastening components 84 and 85 each comprise complementary hook type fasteners. Although the illustrated embodiments show the back waist region 24 overlapping the front waist region 22, which is convenient, the training pant 20 can also be configured so that the front waist region overlaps the back waist region.

In other embodiments contemplated by this invention, fasteners 82-85 can be located anywhere over the front or back regions 22 and 24 of the pant. The fasteners 82-85 can be integral with any of the materials on the pant in the front or back regions 22 and 24. The fasteners can be integral with the entire outer cover of the pant (e.g. in a one piece outer cover product) or integral to the entire liner in the pant, or integral to both the outer cover and liner. The fasteners can be integral to panels 34 and/or 134. Any of the fastening components 82-85 can comprise a stretchable nonwoven loop material.

Hook type fasteners typically comprise a fabric or material having a base or backing structure and a plurality of hook members extending upwardly from at least one surface of the backing structure. The hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of polyamide, polypropylene, polyethylene, or another suitable material. Suitable single-sided hook materials for the fastening components 82-85 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

In accordance with the present invention, the loop type fastener is preferably made of a laminate which has been post bonded as described herein. With particular reference to FIG. 3, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. Alternatively, fasteners 82 and 83 may comprise a single fastener located on the front of the product. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 2, the second fastening components 84 and 85 are desirably although not necessarily disposed on the outer surface 30 of the training pant 20 in the front waist region 22. The second fastening components 84 and 85 are sized to receive the first fastening components 82 and 83 and are desirably positioned along the distal edges 68 of the front side panels 34, and abutting or adjacent to the waist end edge 72. In certain embodiments, for example, the second fastening components 84 and 85 can be located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks. The loop fastening components can be integral with the side panels or adhered to the side panels 34 and 134 by any means known to those skilled in the art such as adhesive bonds, sonic bonds or thermal bonds. The loop fastening components can be extensible and bonded to components of the body 32 in a manner that retains extension and retraction characteristics of the loop fastening components.

The fastening components are desirably rectangular, although they may alternatively be square, round, oval, curved or otherwise non-rectangular in shape. In particular embodiments, each of the fastening components 82-85 defines a length dimension aligned generally, but not necessarily, parallel with the longitudinal axis 48 of the training pant 20 and a width dimension aligned generally, but not necessarily, parallel with the transverse axis 49 of the training pant. For a child of about 9 to about 15 kilograms (20-33 pounds), for example, the length dimension of the fastening components is desirably from about 5 to about 13 centimeters, such as about 10 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82-85 are releasably engaged, the side edges 36 of the absorbent body 32 in the crotch region 26 define the leg openings 52, the waist edges 38 and 39 of the absorbent body, including the waist end edges 72 of the side panels, define the waist opening 50, and the waist regions 22 and 24 jointly define a waistband 75 and hip section 77. For improved formation of the leg openings 52, it can be desirable in some embodiments for the front side panels 34 to be longitudinally spaced from the back side panels 134 (see FIGS. 2 and 3). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82-85 form refastenable seams 88 (FIG. 1) that desirably although not necessarily extend substantially the entire distance between the waist opening 50 and the leg openings 52. More specifically, the refastenable seams 88 can cover about 70 to 100 percent, and particularly about 75 to about 95 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82-85 can be formed to cover about 80 to 100 percent, and more particularly about 85 to about 95 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

It is also contemplated that the fastening components 82-85 may be incorporated as integral portions of the pant rather than separate components applied during manufacture. If the separate fastening components 82 and 83, are manifested as a single unitary fastening component integral with the pant in the front region 22, for example, the size and the shape of the fastening component is directly equal to the size and shape of that region. If the fastening components 82-85 are integral parts of side panels 34 and/or 134, for another example, the fastening components are the same size and shape as the side panels 34 and/or 134.

For the refastenable seams 88 to be located at the sides of the wearer, it can be particularly desirable for the transverse distance between the first fastening components 82 and 83 to be substantially equal to the transverse distance between the second fastening components 84 and 85. The transverse distance between a set of fasteners is the distance measured parallel to the transverse axis 49 between the longitudinal centerlines of the fasteners, measured with the pants 20 laid flat as shown in FIG. 3 and the side panels 34 and 134 in their relaxed, or non-extended, condition. It is also acceptable for fasteners 82 and 83 to have a different width between center lines than fasteners 84 and 85. In another embodiment, the training pant 20 includes only a single unitary second fastening component disposed in the front waist region 22 for refastenably connecting the first fastening components 82 and 83 (not shown).

Figure 4:
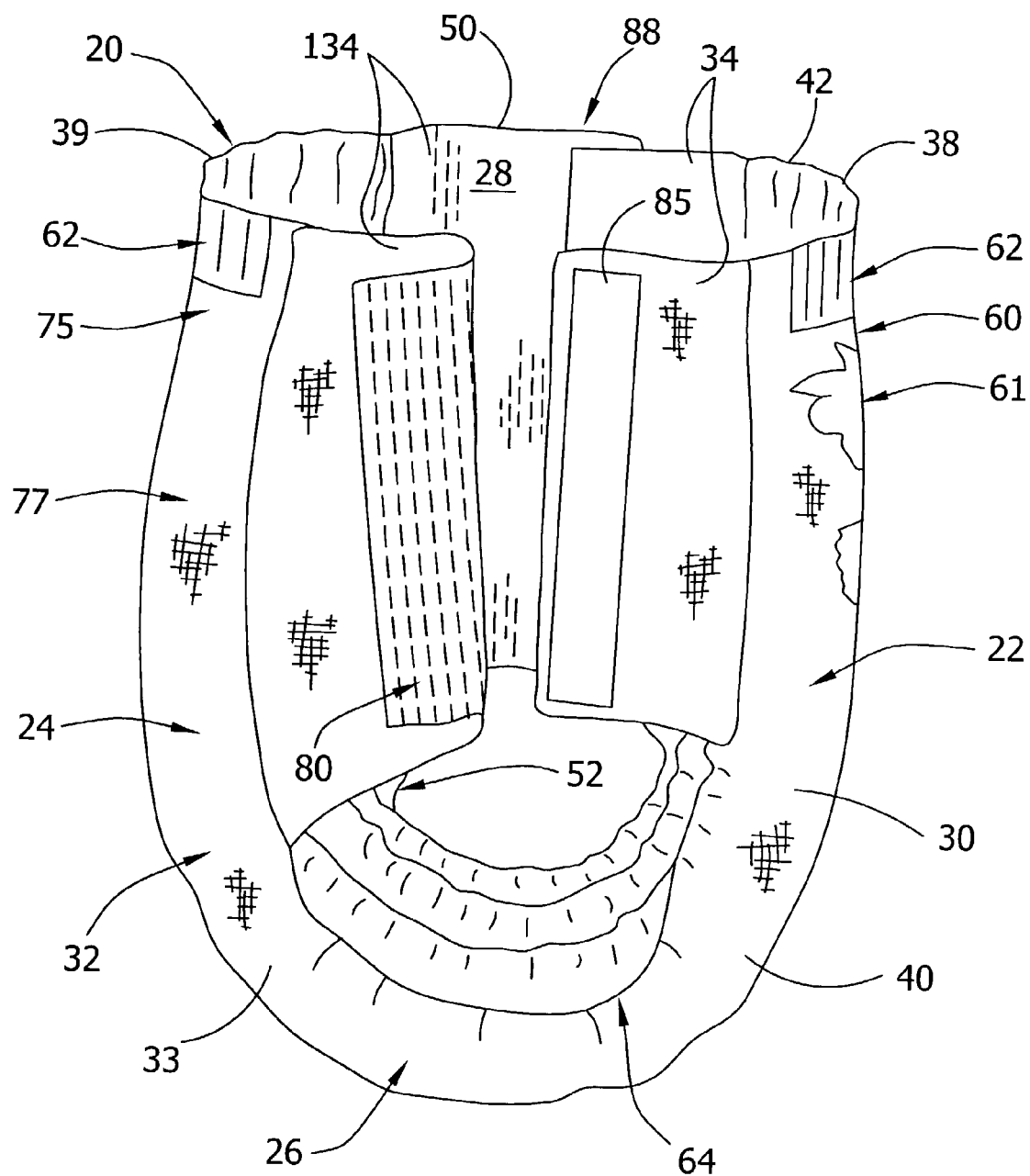
FIG. 4 illustrates an alternative embodiment of the present invention in a side view similar to FIG. 1.
Figure 5:
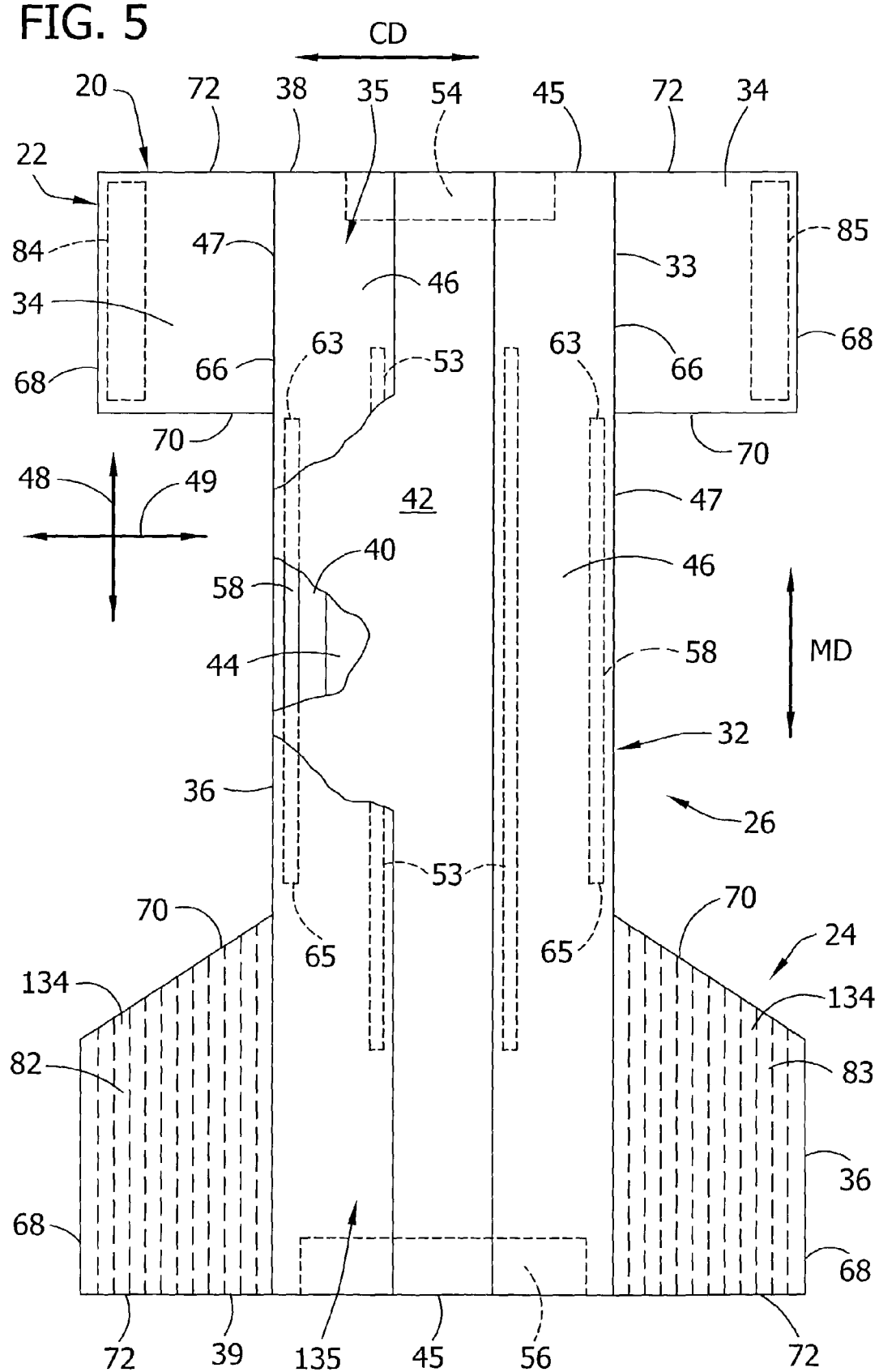
FIG. 5 is a plan view of the embodiment of FIG. 4 in a similar position as FIG. 3.

In a further embodiment illustrated in FIGS. 4 and 5, one or both of the fastening components can comprise integral portions of the waist regions. For instance, the front and back side panels 34 and 134, or portions thereof, can function as fastening components in that they can comprise a material that is releasably engageable with complementary fastening components disposed in the opposite waist region. As illustrated in FIGS. 4 and 5, the side panels 134 can be made of stretchable nonwoven loop material. These side panels could be made of stretchable nonwoven loop material only at their outer edges where they will engage the hook material, and the remainder of the side panels can be made of some other, preferably extensible, material and joined along abutting edges thereof (not shown).

This invention preferably uses a loop material laminate constructed from a nonwoven facing secured to an elastic or inelastic substrate which together have been post bonded to provide fiber loops accessible to the hook material and with sufficient integrity to withstand engagement and disengagement. It is believed that the post bonding provides additional z-directional strength to the resulting composite such that disengagement of the hook material reduces the disruption of the facing or laminate structures, allowing the fastener to be releasable and refastenable. It is also believed that the post bonding enhances durability in use, for example, during application, such that the fastener does not become accidentally disengaged by rupture of the facing or laminate structure.

The loop material laminate can be formed by various methods, including those specifically described herein and combinations and permutations thereof. For instance, the loop material laminate can be formed by elongating an extensible substrate, which may be elastic or inelastic, in one or more directions and bonding the elongated substrate to a nonwoven web of loop material. The substrate can for example be elongated in both a machine direction and a cross machine direction. The nonwoven web can be ungathered, gathered in one direction, or gathered in multiple directions. In particular embodiments, the loop material laminate can comprise a generally ungathered nonwoven web stretch-bonded to an elastomeric substrate. Additionally, the loop material laminate can be formed by pregathering a nonwoven web of loop material and bonding the pregathered nonwoven of loop material to an unstretched elastic or inelastic substrate having elongation characteristics in a direction other than or besides the direction of gathering. The nonwoven web can be gathered by any suitable means, such as creping, necking, use of retractive materials, or the like. Suitable retractive materials for use as a substrate for gathering the nonwoven web or composite can comprise any material adapted to retract upon activation, whether immediately upon activation or subsequently thereto. The retractive material can comprise elastomeric or nonelastomeric materials. Suitable nonelastomeric retractive materials can comprise without limitation polyether block amides (PEBAX®) or the like, and laminates thereof. Suitable elastomeric retractive materials can comprise without limitation LYCRA® materials, elastomeric materials including latex rubber or synthetic urethanes, or the like, and laminates thereof. In particular embodiments, the retractive material can comprise an elastomeric material having an unstable state relative to some other stable and elastic state. In such embodiments, the retractive material can but need not have elastomeric properties in the unstable state. Other exemplary retractive materials are described in PCT publication WO 01/87206 dated Nov. 22, 2001, which is incorporated herein by reference.

In one preferred embodiment, the loop material is a nonwoven laminate material made by (1) laminating a nonwoven web or facing of loop material to an elongated inelastic substrate and (2) post bonding the resultant laminate in a relaxed or semi-relaxed state. Post bonding the laminate provides additional z-directional strength in the post bonded area.

In another preferred embodiment, the loop material is a neck-stretched elastic laminate material made by (1) elongating a nonwoven facing in the machine direction while allowing it to neck down in the cross direction (i.e., "neck stretching"), (2) laminating the resulting necked facing to an elastic substrate while it is elongated in the machine direction and (3) post bonding the resultant laminate in a relaxed or semi-relaxed state. The necking of the facing provides the ability for the material to be extended in the cross direction to about its pre-necked width. This also orients the fibers in the machine direction, which provides an increase in fiber loops available in the cross direction of the material. The stretch-bonding laminating process takes the necked facings and attaches them to a stretched elastic material. The stretched elastic material then gathers the nonwoven facing in the machine direction when the stretching force is released. This gathering then creates a higher density of fibers in the machine direction. Post bonding the relaxed or semi-relaxed laminate as a subsequent third step may or may not interfere with the extension and retraction of the laminate, depending on the bond pattern and area covered. Thus, post bonding provides additional z-directional strength over the entire post bonded area, and the bond pattern may be chosen so as to minimize or maximize the effect of post bonding on the stretch characteristics of the laminate in the post bonded area. This sequence of process steps takes a flat, two-dimensional facing and forms a multi-directional stretchable nonwoven loop material.

In another preferred embodiment, the loop material is a unidirectional stretchable elastic laminate material made by (1) creping a nonwoven facing in the machine direction, (2) laminating the resulting creped facing to an elastic substrate in a relaxed state and (3) subsequently post bonding the resultant laminate in a relaxed or semi-relaxed state. The creping of the facing provides the ability for the material to be extended in the machine direction to about its pre-creped length. The laminating process takes the creped facings and attaches them to an elastic material. Post bonding the relaxed or semi-relaxed laminate as a subsequent third step may or may not interfere with the extension and retraction of the laminate. Thus, post bonding provides additional z-directional strength affecting only the post bonded area, and the bond pattern may be chosen so as to minimize or maximize the effect of post bonding on the stretch characteristics of the laminate. This sequence of process steps takes a flat, two-dimensional facing and forms a unidirectional stretchable loop material.

In yet another preferred embodiment, the loop material is an extensible laminate material made by (1) laminating a nonwoven facing to an elastic or inelastic substrate in a relaxed state, (2) mechanically straining the laminate, and (3) subsequently post bonding the pre-strained laminate in a relaxed or semi-relaxed state. In this embodiment, the laminate is subjected to mechanical manipulation in order to provide a "zero strain" stretch laminate, as described in U.S. Pat. No. 5,628,741 to Buell, et al, hereby incorporated by reference, that is subsequently post bonded as described herein. This sequence of process steps takes a flat, two-dimensional facing and forms an extensible loop material.

In yet a further preferred embodiment, the loop material is a retractable material as described above which can, for example, be bonded to a substrate which is subsequently retracted such as by the application of heat after the laminate is formed. Post bonding is then applied to the laminate before or after retraction.

One embodiment of the loop material utilized in the fastening system of the present invention can be manufactured as set forth in U.S. Pat. No. 5,116,662 to Morman, incorporated herein by reference thereto, and then post bonded as described herein. For example, the neckable material is a nonwoven web of fibers, which should be joined by interfiber bonding to form a coherent web structure which is able to withstand necking. Interfiber bonding may be produced by entanglement of individual meltblown fibers. The fiber entangling is inherent in the meltblown process but may be generated or increased by processes such as, for example, hydraulic entangling or needlepunching. Alternatively and/or additionally thermal bonding or a bonding agent may be used to increase the desired coherence of the web structure.

A gathered nonwoven facing may be made by taking a suitable nonwoven material and elongating it in one or more directions, and causing the web to neck or narrow in the direction(s) perpendicular to the direction(s) of elongation. The nonwoven material used to form the gathered nonwoven facing can be made in accordance with the teachings of U.S. Pat. No. 4,965,122 to Morman, incorporated herein by reference thereto. Suitable nonwoven material may be formed by known nonwoven processes, such as, for example, meltblowing processes, spunbonding processes or bonding and carding a nonwoven web. If the nonwoven material is a web of meltblown fibers, it may include meltblown microfibers.

Gathering of the nonwoven facing can be accomplished by neck-stretching of the material. Any material that can be extended upon application of a force so as to cause it to narrow in the transverse direction of application of the force is suitable for neck-stretching. A necked material can be made into a neck-bonded laminate as taught in U.S. Pat. No. 4,981,747 to Morman. A necked material may also be treated while necked to instill a memory into the material to cause the material to retract from its extension as taught in U.S. Pat. No. 4,965,122 to Morman. One such method of treatment is the application of heat. Certain polymers such as, for example, polyolefins, polyesters and polyamides may be heat treated under suitable conditions to impart such memory. Exemplary polyolefins include one or more of polyethylene, polypropylene, polybutene, ethylene copolymers, propylene copolymers and butene copolymers. Polypropylenes that have been found useful include, for example, polypropylene available from the Himont Corporation under the trade designation PC-973, polypropylene available from the Exxon Chemical Company under the trade designation Exxon 3445, and polypropylene available from the Shell Chemical Company under the trade designation DX 5A09. Chemical characteristics of these materials are available from their respective manufacturers.

The nonwoven material used to form the nonwoven facing could be a multilayer material having, for example, at least one layer of spunbonded web joined to at least one layer of meltblown web, bonded carded web or other suitable material. For example, the nonwoven material may be a multilayer material having a first layer of spunbonded polypropylene having a basis weight from about 0.2 to about 8 ounces per square yard (osy), a layer of meltblown polypropylene having a basis weight from about 0.2 to about 4 osy, and a second layer of spunbonded polypropylene having a basis weight of about 0.2 to about 8 osy. Alternatively, the nonwoven facing may be a single layer of material such as, for example, a spunbonded web having a basis weight of from about 0.2 to about 10 osy or a meltblown web having a basis weight of from about 0.2 to about 8 osy.

The nonwoven facing may also be a composite material made of a mixture of two or more different fibers or a mixture of fibers and particulates. Such mixtures may be formed by adding fibers and/or particulates to a gas stream in which meltblown fibers are carried so that an intimate entangled commingling of meltblown fibers and other materials, e.g., wood pulp, staple fibers or particulates such as, for example, super-absorbent materials occurs prior to collection of the fibers upon a collecting device to form a coherent web of randomly dispersed meltblown fibers and other materials such as disclosed in U.S. Pat. No. 4,100,324 to Anderson et al., the disclosure of which is hereby incorporated by reference.

The base material for the laminate may be made from any material which may be manufactured in sheet form. Generally, any suitable elastomeric or plastic fiber forming resins or blends containing the same may be utilized for the fibers, threads, filaments, and/or strands or the nonwoven webs of fibers, threads, filaments, and/or strands of the invention and any suitable film forming resins or blends containing the same may be utilized for the base films of the invention. Useful base sheets may have basis weights ranging from about 5 gsm (grams per square meter) to about 300 gsm, for example, from about 5 gsm to about 150 gsm.

Exemplary inelastic base materials for this invention include polyolefin films, particularly polyethylene or polypropylene films and blends thereof. Particularly for laminates in which the base material will be mechanically strained, either before or after lamination, the base material should be one that can be subjected to elongation without undue rupturing or tearing. Thus, it is preferred that an inelastic material have an ultimate elongation to break of at least about 400% to about 700% in the direction of elongation as measured using a method consistent with ASTM D-638. Thus, preferred polymeric films for use as an inelastic base material contain a high content of linear low density polyethylene. Particularly preferred materials for the base sheet include blends comprised of about 45-90% linear low density polyethylene and about 10-55% polypropylene.

Exemplary films for use as the base material for the laminates of the present invention are manufactured by Tredegar Industries, Inc. of Terre Haute, Ind. under the designation RR8220 blend for blown films and RR5475 blend for cast films.

Exemplary elastic base materials for the laminates of this invention may be made from block copolymers having the general formula A-B-A' where A and A' are each a thermoplastic polymer endblock which contains a styrenic moiety such as a poly (vinyl arene) and where B is an elastomeric polymer midblock such as a conjugated diene or a lower alkene polymer. The elastic sheet may be formed from, for example, (polystyrene/poly(ethylenebutylene)/polystyrene) block copolymers available from the Shell Chemical Company under the trademark KRATON G. One such block copolymer may be, for example, KRATON™ G-1657.

Other exemplary elastomeric materials which may be used to form elastic sheet include polyurethane elastomeric materials such as, for example, those available under the trademark ESTANE from B. F. Goodrich & Co., polyamide elastomeric materials such as, for example, those available under the trademark PEBAX from the Rilsan Company, and polyester elastomeric materials such as, for example, those available under the trade designation Hytrel from E. I. DuPont De Nemours & Company. Formation of elastic sheets from polyester elastic materials is disclosed in, for example, U.S. Pat. No. 4,741,949 to Morman et al., hereby incorporated by reference. Elastic sheet may also be formed from elastic copolymers of ethylene and at least one vinyl monomer such as, for example, vinyl acetates, unsaturated aliphatic monocarboxylic acids, and esters of such monocarboxylic acids. The elastic copolymers and formation of elastic sheets from those elastic copolymers are disclosed in, for example, U.S. Pat. No. 4,803,117.

Processing aids may be added to the elastomeric polymer. For example, a polyolefin may be blended with the elastomeric polymer (e.g., the A-B-A elastomeric block copolymer) to improve the processability of the composition. The polyolefin must be one which, when so blended and subjected to an appropriate combination of elevated pressure and elevated temperature conditions, is extrudable, in blended form, with the elastomeric polymer. Useful blending polyolefin materials include, for example, polyethylene, polypropylene and polybutene, including ethylene copolymers, propylene copolymers and butene copolymers. A particularly useful polyethylene may be obtained from the U.S.I. Chemical Company under the trade designation Petrothene NA 601 (also referred to herein as PE NA 601 or polyethylene NA 601). Two or more of the polyolefins may be utilized. Extrudable blends of elastomeric polymers and polyolefins are disclosed in, for example, U.S. Pat. No. 4,663,220 to Wisneski et al., hereby incorporated by reference. The elastic sheet of base material may also be a pressure sensitive elastomeric adhesive sheet.

The elastic sheet of base material may also be a multilayer material in that it may include two or more individual coherent webs and/or films. Additionally, the elastic sheet may be a multilayer material in which one or more of the layers contain a mixture of elastic and inelastic fibers or particulates. As an example of the latter type of elastic web, reference is made to U.S. Pat. No. 4,209,563, incorporated herein by reference, in which elastomeric and non-elastomeric fibers are commingled to form a single coherent web of randomly dispersed fibers. Another example of such an elastic composite web would be one made by a technique such as disclosed in previously referenced U.S. Pat. No. 4,741,949. That patent discloses an elastic nonwoven material which includes a mixture of meltblown thermoplastic fibers and other materials. The fibers and other materials are combined in the gas stream in which the meltblown fibers are borne so that an intimate entangled commingling of meltblown fibers and other materials, e.g., wood pulp, staple fibers or particulates such as, for example, hydrocolloid (hydrogel) particulates commonly referred to as super-absorbents occurs prior to collection of the fibers upon a collecting device to form a coherent web of randomly dispersed fibers.

Nonwoven facing may be joined to one or both sides of the base material in at least three places by any suitable means such as, for example, thermal bonding or ultrasonic welding to form the laminate prior to post bonding.

With regard to thermal bonding, one skilled in the art will appreciate that the temperature to which the materials, or at least the bond sites thereof, are heated for heat-bonding will depend not only on the temperature of the heated roll(s) or other heat sources but on the residence time of the materials on the heated surfaces, the basis weights of the materials and their specific heats and thermal conductivities. However, for a given combination of materials, and in view of the herein contained disclosure, the processing conditions necessary to achieve satisfactory bonding can be readily determined.

Alternatively, the nonwoven facing and the base material may be joined by using other bonding methods and materials such as, for example, adhesives, pressure sensitive adhesives, solvent welding, hydraulic entangling, high energy electron beams, and/or lasers.

For purposes of the present invention, shear strength values are determined using the following shear test, which simulates the forces put on a hook and loop system during product use. Testing can be done in any direction of the hook and loop system.

Reported shear values are derived from testing the fastening system in a direction parallel to the transverse axis of the product, when the fastening system is installed in a product.

Test Method: Shear Strength

Test Procedure

This procedure is a tensile bench test to measure the shear force required to separate a mechanical fastening system that joins two materials. The shear force of separation is measured by determining load values as the two materials are pulled apart parallel to their plane of contact. The shear strength test values are an indication of how well the mechanical fastening system stays engaged against in-plane shear force. The sample is pulled in the tensile tester until the sample pulls apart. Shear strength is the peak load result.

1. Overview

A material sample of two material layers joined by a mechanical fastening system such as a hook and loop system is assembled. The fastening system joins two pieces of material that overlap in the landing area. The sample is prepared by aligning and applying the hook material to the loop material, and by rolling a 2000 gram weight over the fastening system to engage the fastener. The sample is then placed between clamps on a tensile tester. One piece of material is held in the upper clamp, while the other is held in the lower clamp. The fastening system is arrayed between the clamps, approximately parallel to the edges of the clamp faces. The width of all materials to be tested is 3 inches (76.2 mm). The gage length is 2 inches (50.8 mm) between the edges of the clamp faces. The term "load" refers to the gram value measured by the load cells in the tensile tester.

The jaws are separated at a controlled rate until the fastening system is pulled apart. The load values generated on the material throughout this process are recorded. The peak load value is recorded as the shear strength of the fastening system.

Peak load values for samples of non-standard widths should be normalized by multiplying or dividing by the factor by which the sample width deviates from 3 inches (76.2 mm). For example, the peak load value derived by pulling apart a 1 inch (25.4 mm) wide sample should be multiplied by 3.

Suitable materials include hook and loop fastening systems, which may comprise or be attached to materials used to form the disposable garments described herein.

2. Apparatus and Materials 2.1 Constant Rate of Extension (CRE) tensile tester such as an MTS tensile tester model SYNERGIE™ 200 Test Bed; available from MTS Systems Corporation, Research Triangle Park, N.C. USA.

2.2 Load cells: A suitable cell selected so the majority of the peak load values fall between 10% and 90% of the manufacturer's recommended ranges of load cell's full scale value; for example, Model 100N available from MTS Systems Corporation, Research Triangle Park, N.C. USA.

2.3 Operating software and data acquisition system such as MTS TestWorks® for Windows software version 4; available from MTS Systems Corporation, Research Triangle Park, N.C. USA.

2.4 Grips: pneumatic-action grips, top and bottom, identified as part number 38.00716 available from MTS Systems Corporation.

2.5 Grip faces: 25 by 75-mm (1 by 3-inch) interlocking faces such as are available from MTS Systems Corporation.

2.6 Mechanical roller such as Rolldown, modified to be able to provide 2 kilograms of pressure during the rolling sequence; available from ChemInstruments, Fairfield, Ohio, USA.

3. Conditioning

Reasonable ambient conditions are required for testing. The instruments used should be calibrated as described in the manufacturer's instructions for each instrument.

4. Test Specimen (FIGS. 12 and 13)

The hook material 300 to be tested may be mounted on other components of the disposable garments described herein, such as on side panel material. The hook material 300 may be attached using any suitable method, such as by adhesive or ultrasonic bonding. The sample of hook material 300 is prepared so that the length of the hook area mounted to the underlying material 302 is at least 4 inches (101.6 mm). The width of the hook material—side panel material composite 304 should be at least about 3 inches (76.2 mm). The hook material 300 should be located along or near one longitudinal edge of the composite 304. The composite material 304 is positioned on a flat surface so that the hook material 300 runs side-to-side and is located at the composite edge nearest the tester.

The loop material 306 is placed over the hook composite material 304 so that the loop material completely covers the hook material 300. The loop material 306 is placed inward of the hook composite 304 (closer to the tester than the hook composite), so that the upper edge of the loop material 306 overlaps the upper edge of the hook material 300 by about 4 mm. The loop material 306 should also be at least about 3 inches (76.2 mm) in width, so that the total width of the joined materials (perpendicular to the length of the fastening area) should be at least about 4.5 inches (114.3 mm). The joined materials should not be handled or pressed in the landing area 308.

The joined materials are then trimmed at both ends so that the landing area is 3±0.04 inches (76.2±1 mm) in length. The landing area 308 should be essentially perpendicular to the trimmed edges; the trimmed edges should be parallel.

Figure 14:
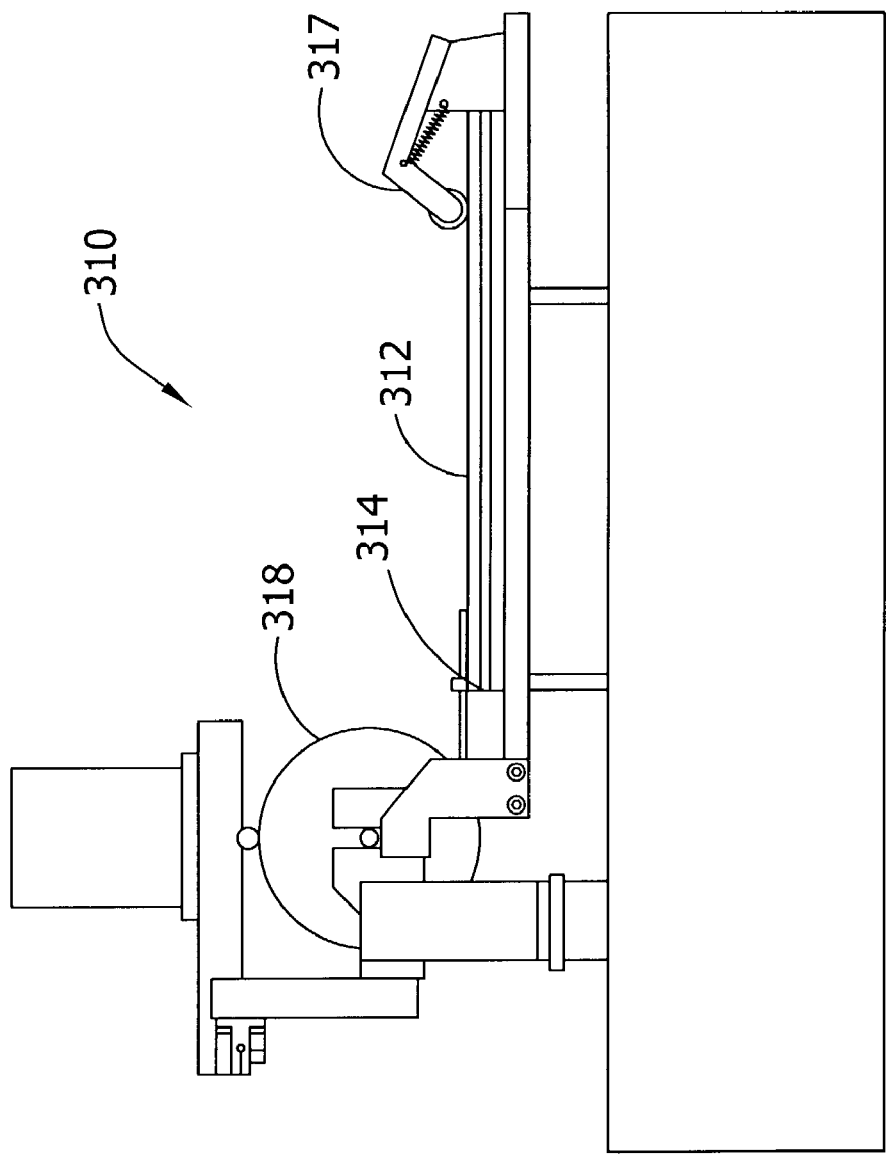
FIG. 14 is a side elevational schematic view of a mechanical rolling mechanism used in testing specimens.

The specimen is placed into a mechanical rolling device 310 shown in FIG. 14 so that the specimen lies under a clamp 312, with one trimmed edge against the clamp base 314, with the hook material 300 side down. The centerline 316 of the landing area 308 should be aligned with the centerline of the face of the roller 318. Lower the clamp 312 and engage a latch 317. Press START to initiate the rolling sequence. The mechanical roller 318 should be calibrated to apply a 2 kilogram weight during rolling, and should stop off of the hook material 300 after the first cycle. The roller 318 should move at a speed of 100 inches (250 cm) per minute. The specimen is rolled twice using the roller 318.

The clamp 312 of the mechanical roller 310 is raised and the sample is gently removed without touching the landing area 308.

The specimen is tested using the tensile test procedure that follows; the specimen is tested along the direction indicated by the arrows in FIGS. 12 and 13. At least four specimens of each sample should be tested, and the results averaged.

5. Procedure

| Tensile Tester test conditions: | |
|---|---|
| Break sensitivity | 60% |
| Break threshold | 0.5 pounds of force |
| Preload? | No |
| Test speed | 500 mm/min |
| Gage length: | 2 inches (50.8 mm) |
| Number of cycles: | 1 |

A. Using the tensile frame pushbutton controls for crosshead position, move grips to provide a gage length of 2 inches (50.8 mm). Tare the crosshead channel to this initial gage length.

B. Without touching the fastening area, place a material specimen so that the fastener is centered (vertically) between the grips, held in a centered position (horizontally) within each grip, and oriented correctly (3 inch/76.2 mm dimension running the width direction on the grips). The specimen's vertical edges should be perpendicular to the nearest edges of the grip faces, and the fastener should be parallel to the edges of the faces. The arrows in FIGS. 12 and 13 show the direction in which the sample is pulled during the test.

C. Close the upper grips on the specimen and tare the load channel.

D. Hold the specimen in such a way as to minimize slack in the specimen, but do not place the specimen under tension, and close the lower grips on the specimen.

E. Run the test using the above parameters by clicking on the RUN button.

F. When the test is complete, save the data to a sample file.

G. Remove the specimen from the grips.

H. Run additional specimens of a given sample using steps B-E and G; the data for all specimens should be saved to a single file.

I. Continue testing all samples in this manner.

J. Data are reported as the average peak load value for each sample.

Post bonding with the above described materials in accordance with the present invention may or may not restrict the retraction or extension of the material as occurs when post bonding is done during making of the elastic material. Post bonding can be limited to the landing area for the mating fastening component, or it can be an overall bond pattern to cover the entire laminate surface, or it can be a segmented or partitioned combination of bond patterns covering part or all of the laminate. Post bonding of these materials after their initial construction and lamination can improve their cohesive strengths and the integrity of facing layers while having little impact on their overall gathered strength or stretch characteristics. Tests have shown that post bonding of a stretch bonded laminate increases the shear test strength from 2000 grams to 3000 grams for a hook to loop shear test.

Prior art laminate materials, not post bonded in accordance with the present invention, have shown a tendency to delaminate when used as a loop material when worn by a child. By post bonding these materials, delamination is less likely to occur.

Almost any bond pattern can be used to post bond the laminate in accordance with the present invention, including patterns consisting of arrays of dots, diamonds, lines, and other discontinuous shapes arranged in rows and columns. Also contemplated for this invention are continuous patterns, such as crosshatched lines, intersecting sine waves, and the like.

Figure 6:
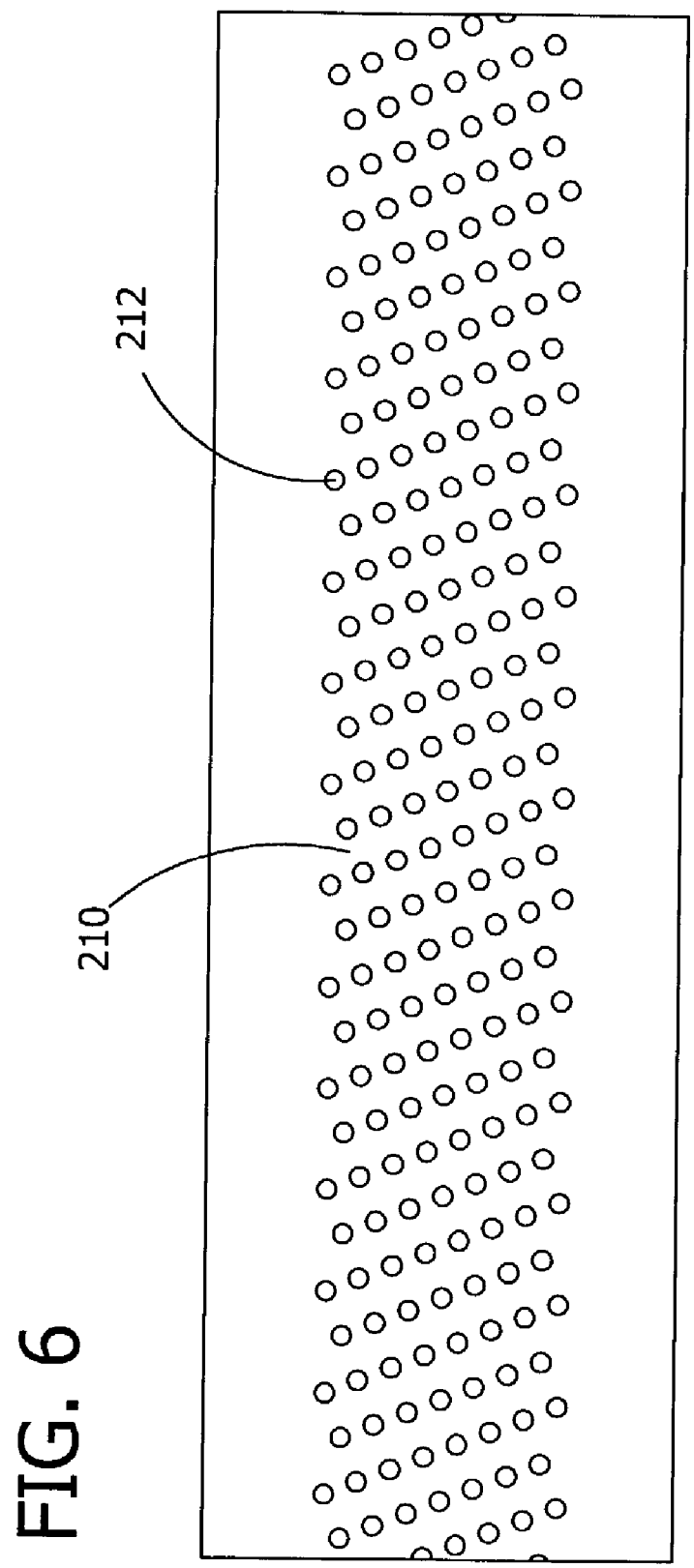
FIGS. 6, 7, and 8 illustrate examples of bond patterns useful for post bonding as described in the present invention.

An example of a useful bond pattern is shown in FIG. 6, which could be created by an ultrasonic anvil with corresponding raised areas. The bond pattern 210 has round bond points 212 with about 0.042 inch diameter, with a density of 33 points per square inch, providing a bond area in the material of approximately 5%. Post bonding extensible or stretchable nonwoven loop laminates with such a bond pattern, in which the bond area is less than about 15%, is especially useful in preventing failure of the mechanical fastening system by delamination of the loop material without substantially inhibiting extension or recovery of the material.

Figure 7:
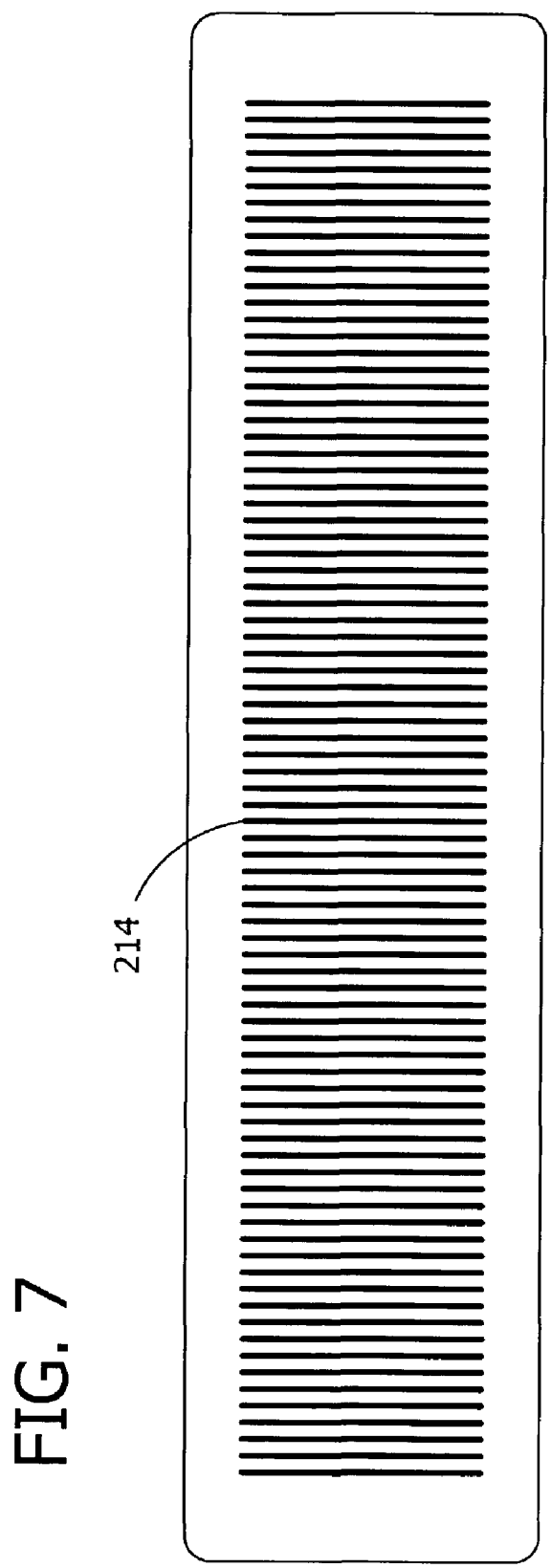

Another example of a suitable bond pattern according to the present invention is shown in FIG. 7, consisting of rectangular bars 214 of 0.031 inch width and 0.941 inch length with a density of 14.2 bars per lineal inch of length, providing a bond area of approximately 45%. Post bonding nonwoven loop laminates with such a bond pattern, in which the bond area is greater than about 25%, is also useful in preventing failure of the mechanical fastening system by delamination of the loop material, and can result in a significant increase in the shear strength of the system and a significant reduction in the stretch and recovery in the landing area.

Figure 8:
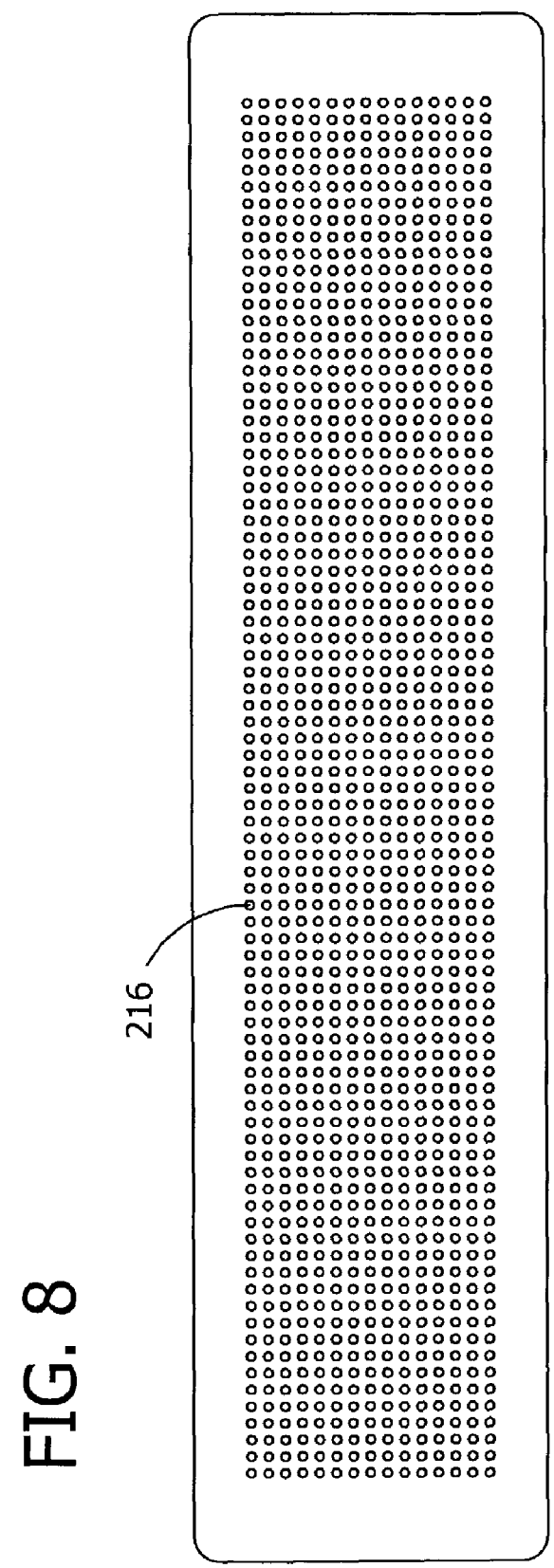

A third example of a suitable bond pattern according to the present invention is shown in FIG. 8, consisting of round bond points 216 of 0.047 inch diameter with a density of 168 points per square inch, providing a bond area of approximately 15%. This intermediate bond area, and bond areas in general in the range of 15% to 25%, can result in a significant increase in the z-directional strength of the laminate and its ability to withstand disengagement without damage, with a moderate effect on stretch and recovery of the laminate in the landing area.

In one form the post bonded loop laminate area forms a portion of a loop fastening component which is about 25% of the landing area of that component. Depending on what combinations of properties of stretch, strength and elasticity are desired, as discussed above for various densities of bond points in the post bonding process, the bond density, the portion of the laminate which is actually bonded by the bond pattern, is desirably between 1% and 75% in the post bonded loop laminate portion of the first fastening component.

Figure 10:
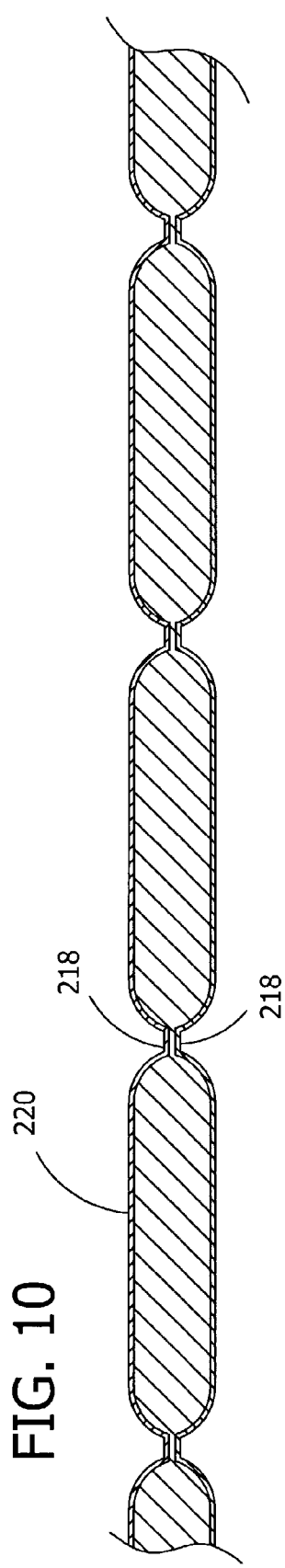
FIG. 10 is a schematic illustration of a cross-sectional view through a post bonded laminate in accordance with the present invention.
Figure 11:
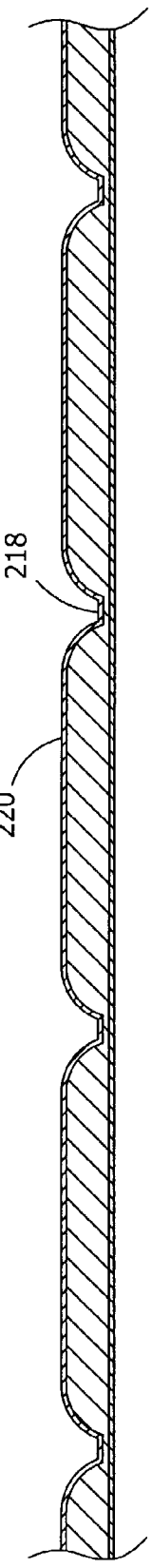
FIG. 11 is a schematic illustration of a cross-sectional view through a post bonded laminate with a slightly different structure than that shown in FIG. 10, also in accordance with the present invention.

The resulting post-bonded material is illustrated in cross-section in FIGS. 10 and 11 where the post-bonding occurs in valleys 218 in the laminate 220. The pattern shown in FIG. 10 could be formed by either thermal bonding or ultrasonic bonding while the pattern shown in FIG. 11 is more typical of, but not exclusive to, a thermal bonding process.

As an example of the application of this invention, an elastic laminate prepared by elongating elastic filaments and securing nonwoven facing to the filaments by means of an adhesive was post bonded with the pattern shown in FIG. 6. Similar shear strengths of hook engagement were obtained, in the range of 3300 to 3500 grams, when the material was evaluated using an exemplary hook material, with and without post bonding, but the samples without post bonding suffered from delamination and would not withstand repeated disengagement. In another example, a mechanically pre-strained laminate with an inelastic film base was post bonded with the bond pattern shown in FIG. 6. In this case shear strength of hook engagement, using the same hook material, was increased from an average of 2700 grams without post bonding to an average of 4400 grams with post bonding. In both of these examples, the laminates were made useable as a loop fastening element in a mechanical fastening system by means of the post bonding step. As can be seen from the above examples, post bonding can enhance shear strength directly, or by enhancing the durability of the laminate, or both. In a preferred form shear strength of the post bonded laminate is preferably in the range of about 1000 to about 5000 grams, and more preferably in the range of about 1500 to about 3500 grams.

Figure 9:
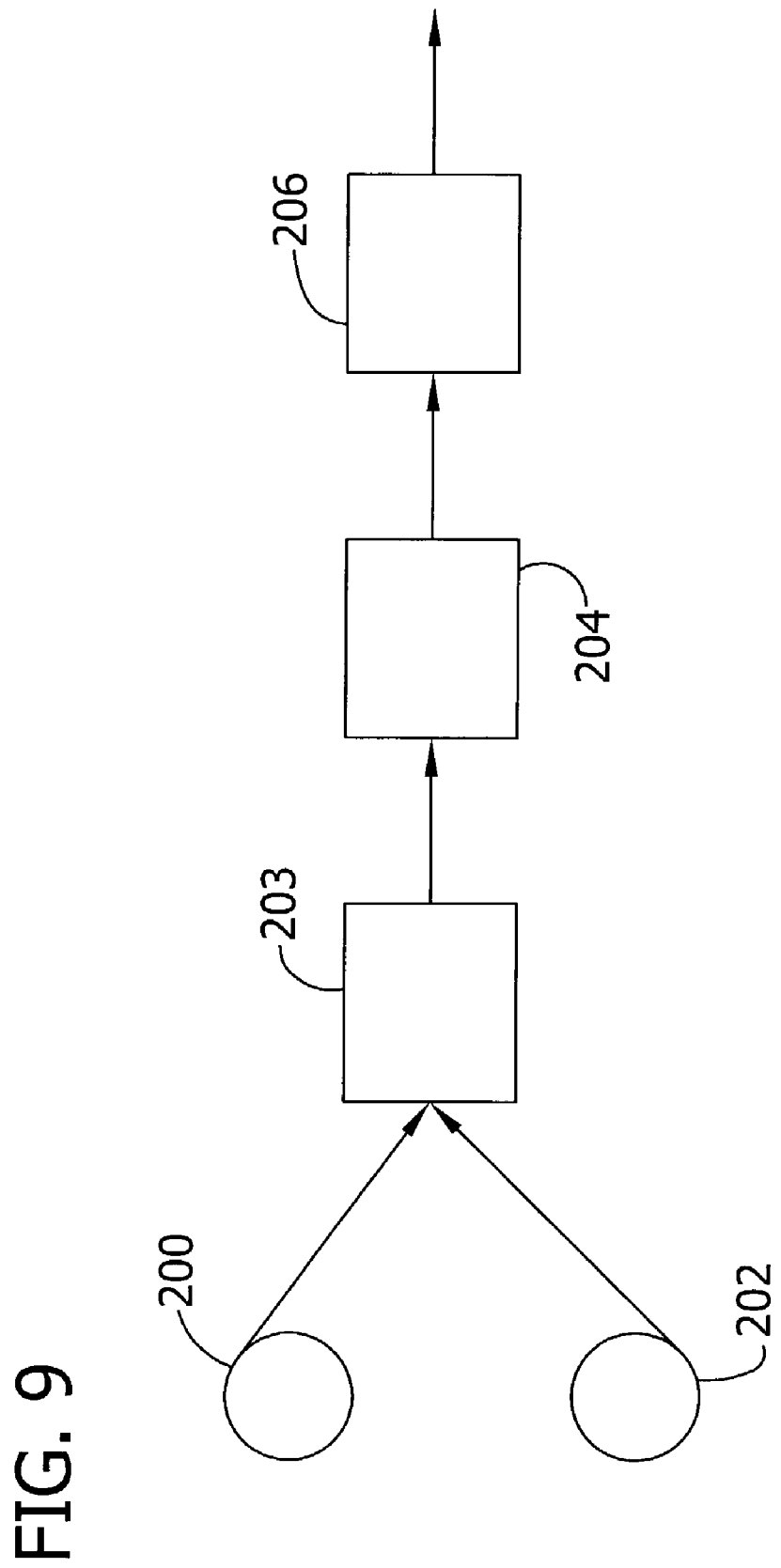
FIG. 9 is a block diagram showing the laminating and bonding process.

The method of manufacturing an article in accordance with the present invention is illustrated in block diagram form in FIG. 9. A supply 200 of nonwoven web, such as those described, is fed to a laminating station 203 where it is laminated to another material coming from a supply 202 in conventional manner as described above. The laminate can then be allowed to retract, either partially or completely in at least one direction, also as described above, and is then post bonded at 206 to form the post bonded laminate of the present invention. Post bonding in accordance with the present invention can be done with conventional techniques, including but not limited to ultrasonic bonding or thermal bonding. The post bonded material can then be supplied to an article construction station to construct an article, such as training pants or the like garment also as discussed above. The stations illustrated in FIG. 9 can be continuous or intermittent and can be combined as desired so long as the above detailed discussion of the process is observed.

It is also contemplated that when the training pants or the like garment are initially constructed and folded by machine, the loop material can be post bonded prior to being positioned over the hook material and then pressed thereon to give an initial construction that is stronger in the mechanical fastener system than conventional mechanical fastening systems.

While the mechanical fastening system of the present invention is shown and described herein in connection with children's toilet training pants, it is understood that such fastening systems may be incorporated into various other disposable absorbent articles, such as diapers, adult incontinence garments, sanitary napkins and the like, as well as surgical bandages and sponges, without departing from the scope of the present invention.

As various changes could be made in the above constructions and methods, without departing from the scope of the invention, it is intended that all matter contained in the above description and shown in the accompanying drawings shall be interpreted as illustrative and not in a limiting sense.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What we claim is:

1. A method of forming a post bonded loop laminate material suitable for use in a hook and loop fastening system for an article comprising: providing a first layer of material comprising a nonwoven web of loop material; laminating the first layer of material to a second layer of material to form a nonwoven loop laminate material; mechanically straining the laminate; and, bonding the first layer of material to the second layer of material after mechanically straining the laminate to form a post bonded loop laminate material.

2. The method of claim 1 wherein the second layer of material has one of extensible properties and elastic properties.

3. The method of claim 2 wherein the second layer of material comprises a nonwoven material.

4. The method of claim 2 wherein the second layer of material comprises strands of material.

5. The method of claim 2 wherein the second layer of material comprises a film.

6. The method of claim 1 where the second layer of material comprises an inelastic material.

7. The method of claim 2 further comprising elongating the second layer of material in the machine direction before lamination.

8. The method of claim 2 further comprising elongating the second layer of material in the cross machine direction before lamination.

9. The method of claim 2 further comprising elongating the second layer of material in both the machine and cross machine direction before lamination.

10. The method of claim 1 further comprising necking down the first layer of material in at least one of a machine direction and a cross machine direction prior to laminating to the second layer of material.

11. The method of claim 10 further comprising applying a force to the first layer of material wherein fibers of the first layer of material are oriented in a direction of the applied force with or without substantially necking the first layer of material in a direction perpendicular to the applied force prior to lamination.

12. The method of claim 10 further comprising thermally treating the first layer of material prior to lamination.

13. The method of claim 1 further comprising prestraining the nonwoven loop laminate material prior to bonding of the first and second layers.

14. The method of claim 1 further comprising sizing an area of the loop laminate material to be bonded, the bonded area being at least 25 percent of the size of an intended landing area for a hook material.

15. The method of claim 1 wherein the post bonded loop laminate material is one of extensible and elastic in at least one direction.

16. The method of claim 1 wherein the post bonded loop laminate material is extensible in a first direction and elastic in a second substantially perpendicular direction.

17. The method of claim 15 wherein the post bonded the loop laminate material has substantially the same extension and retraction characteristics as the nonwoven loop laminate material.

18. The method of claim 15 wherein the post bonded loop laminate material has lower extension and retraction than the nonwoven loop laminate material.

19. The method of claim 1 wherein the bonding step comprises point bonding the first layer of material to the second layer of material.

20. The method of claim 1 further comprises allowing the mechanically strained laminate to relax before bonding the first layer of material to the second layer of material.

* * * * *